United States Patent [19]

Urbahns et al.

[11] Patent Number: 5,652,251
[45] Date of Patent: Jul. 29, 1997

[54] 6-AMINO-1,4-DIHYDROPYRIDINE COMPOUNDS AS MEDICAMENTS FOR TREATMENT OF THE CENTRAL NERVOUS SYSTEM, AND PROCESSES FOR THEIR PREPARATION

[75] Inventors: Klaus Urbahns; Siegfried Goldmann, both of Wuppertal; Hans-Georg Heine, Krefeld; Bodo Junge; Rudolf Schohe-Loop, both of Wuppertal; Henning Sommermeyer, Köln; Thomas Glaser, Overath; Reilinde Wittka, Köln; Jean-Marie-Viktor De Vry, Rösrath, all of Germany

[73] Assignee: Bayer Aktiengesellschaft, Leverkusen, Germany

[21] Appl. No.: 516,597

[22] Filed: Aug. 18, 1995

[30] Foreign Application Priority Data

Aug. 25, 1994 [DE] Germany ............... 44 30 095.6

[51] Int. Cl.$^6$ ............... C07D 471/02; C07D 211/90; C07D 211/92; A61K 31/44
[52] U.S. Cl. ............... 514/353; 514/300; 514/334; 514/344; 546/121; 546/257; 546/289; 546/308
[58] Field of Search ............... 546/121, 257, 546/289, 308; 514/300, 334, 344, 353

[56] References Cited

U.S. PATENT DOCUMENTS 3,867,393  2/1975  Meyer et al. ............... 546/121

FOREIGN PATENT DOCUMENTS 0630895  12/1994  European Pat. Off. .
2210674   9/1973  Germany .

OTHER PUBLICATIONS

Troschütz et al, Arch. Pharm. vol. 326, No. 6, 1993, pp. 335–339.
R. Troschütz, et al., Arch. Pharm. (Weinheim), vol. 324, pp. 73 – 77, (1991).
R. Troschütz, Arch. Pharm. (Weinheim), vol. 322, pp. 285 – 290, (1989).
P.W.L. Tas, et al., Neuroscience Letters, vol. 94, pp. 279 – 284, (1988).
R. Troschütz, et al., Arch. Pharm. (Weinheim), vol. 327, pp. 33 – 40, (1994).
F. Laure, et al., Synthesis, pp. 719 – 720, (1989).
J.C. Ellory, et al., Br. J. Pharmacol., vol. 111, pp. 903 – 905, (1994).
J.C. Ellory, et al., Br. J. Pharmacol., vol. 106, pp. 972 – 977, (1992).
J.C. Ellory, et al., FEBS, vol. 296, No. 2, pp. 219 – 221, (1992).

Primary Examiner—Zinna Northington Davis
Attorney, Agent, or Firm—Sprung Horn Kramer & Woods

[57] ABSTRACT

The present invention relates to the new use of 6-amino-5-nitro- and -5-cyano-1,4-dihydropyridines of the general formula (I)

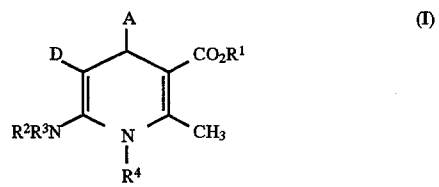

in which

A, D and $R^1$–$R^4$ have the meaning given in the description, new 6-acylamino-dihydropyridines, processes for their preparation and their use as medicaments as selective potassium channel modulators, in particular for treatment of the central nervous system.

16 Claims, No Drawings

6-AMINO-1,4-DIHYDROPYRIDINE COMPOUNDS AS MEDICAMENTS FOR TREATMENT OF THE CENTRAL NERVOUS SYSTEM, AND PROCESSES FOR THEIR PREPARATION

The present invention relates to the new use of 6-amino-5-nitro- and -5-cyano-1,4-dihydropyridines, new 6-acylamino-dihydropyridines, processes for their preparation and their use as medicaments, as selective potassium channel modulators, in particular for treatment of the central nervous system.

Amino-substituted 1,4-dihydropyridines and their calcium-antagonistic actions are already known [in this context, compare Arch. Pharm. 324 (2), 73–7, 1991; Arch. Pharm. 322 (5), 285–90, 1989 and DOS 22 10 674].

It has been found that the 6-amino-5-nitro- and-5-cyano-1,4-dihydropyridines, some of which are known, of the general formula (I)

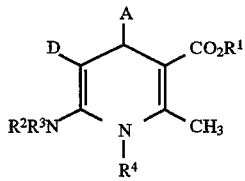

(I)

in which

A represents aryl having 6 to 10 carbon atoms or pyridyl, each of which is optionally substituted up to 3-fold in an identical or different manner by nitro, cyano, phenyl, halogen, trifluoromethyl or by straight-chain or branched alkylthio or alkoxy having in each case up to 6 carbon atoms, D represents cyano or nitro, $R^1$ represents hydrogen, or represents straight-chain or branched alkyl having up to 8 carbon atoms, $R^2$ and $R^3$ are identical or different and represent hydrogen, or represent straight-chain or branched alkyl or acyl having in each case up to 6 carbon atoms, $R^4$ represents hydrogen, or $R^3$ and $R^4$ together represent a radical of the formula —$(CH_2)_n$—, wherein n denotes the number 2, 3 or 4, and physiologically acceptable salts thereof, surprisingly have a selective modulating action on potassium channels and are suitable for use for combatting cerebral diseases and diseases of the Central Nervous System (CNS) and sickle cell anemia.

Physiologically acceptable salts are in general salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid or benzoic acid, or methanesulphonic acid, ethanesulphonic acid, phenylsulphonic acid, toluenesulphonic acid or naphthalenedisulphonic acid.

The compounds according to the invention can exist in stereoisomeric forms, which either behave as mirror images (enantiomers) or do not behave as mirror images (diastereomers). The invention relates both to the antipodes and to the racemic forms, as well as the diastereomer mixtures. The racemic forms, like the diastereomers, can be separated into the stereoisomerically uniform constituents in a known manner.

The use of compounds of the general formula (I) in which

A represents phenyl, naphthyl or pyridyl, each of which is optionally substituted up to 3-fold in an identical or different manner by nitro, cyano, phenyl, halogen, trifluoromethyl or by straight-chain or branched alkylthio or alkoxy having in each case up to 4 carbon atoms, D represents cyano or nitro, $R^1$ represents straight-chain or branched alkyl having up to 6 carbon atoms, $R^2$ and $R^3$ are identical or different and represent hydrogen, or represent straight-chain or branched alkyl or acyl having in each case up to 4 carbon atoms, $R^4$ represents hydrogen, or $R^3$ and $R^4$ together represent a radical of the formula —$(CH_2)_n$—, wherein n denotes the number 2 or 3, and salts thereof, is preferred.

The use of compounds of the general formula (I) in which

A represents phenyl or pyridyl, each of which is optionally substituted up to 2-fold in an identical or different manner by nitro, cyano, phenyl, fluorine, chlorine, trifluoromethyl, methoxy or methylthio, D represents cyano or nitro, $R^1$ represents straight-chain or branched alkyl having up to 4 carbon atoms, $R^2$ and $R^3$ are identical or different and represent hydrogen, or represent straight-chain or branched alkyl or acyl having in each case up to 4 carbon atoms, $R^4$ represents hydrogen, or $R^3$ and $R^4$ together represent a radical of the formula —$(CH_2)_n$—, wherein n denotes the number 2 or 3, and salts thereof, is particularly preferred for combating cerebral diseases.

The compounds of the general formula (I) according to the invention display an unforeseeable, valuable pharmacological action spectrum.

They are channel modulators having a surprising selectivity for large conductance calcium-dependent potassium channels (BK(Ca) channels), in particular the potassium channels of the central nervous system. At the same time, they are distinguished by the absence of a significant calcium channel activity.

On the basis of their pharmacological properties, they can be employed for the preparation of medicaments for treatment of essentially degenerative diseases, such as, for example, with the occurrence of dementias (multiinfarction dementia (MID), primary degenerative dementia (PDD), presenile and senile Alzheimer's disease, HIV dementia and other forms of dementia), Parkinson's disease or amyotropic lateral sclerosis, as well as multiple sclerosis.

The active compounds furthermore are suitable for treatment of age-related disturbances in cerebral performance, organic brain syndrome (OBS) and age-associated memory impairment (AAMI).

They are suitable for the prophylaxis and treatment and for combating the consequences of cerebral circulatory disturbances, such as cerebral ischaemias, apoplexies, craniocerebral traumas and subarachnoid haemorrhages.

They are valuable for treatment of depressions and psychoses, for example, schizophrenia. They are furthermore suitable for treatment of disturbances in neuroendocrine secretion and neurotransmitter secretion, and associated disturbances in health, such as mania, alcoholism, drug abuse, addiction or pathological eating behaviour. Other fields of use are treatment of migraine, sleep disturbances and neuropathies. They are moreover suitable as analgesics.

The active compounds are furthermore suitable for treatment of disturbances in the immune system, in particular T lymphocyte proliferation, and for influencing the smooth musculature, in particular the uterus, urinary bladder and bronchial tract, and for treatment of associated diseases, such as, for example, asthma and urinary incontinence, and for treatment of arrhythmia, angina and diabetes.

The invention furthermore relates to new compounds of the general formula (I)

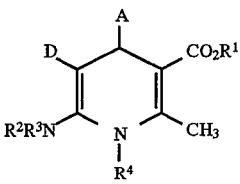
(I)

and salts thereof, with the substituent meanings shown in the following tables:

| D | A | $R^2$ | $R^3$ | $R^4$ |
|---|---|---|---|---|
| $NO_2$ | ![phenyl with CF3 and Cl] | H | H | H |
| $NO_2$ | ![phenyl with Cl and CF3] | $-CO-CH_3$ | H | H |
| $NO_2$ | ![phenyl with Cl and CF3] | H | | $-CH_2-CH_2-$ |
| $NO_2$ | ![phenyl with CF3] | H | H | H |
| $NO_2$ | ![phenyl with CF3] | $-CO-CH_3$ | H | H |
| $NO_2$ | ![phenyl with CF3] | H | | $-CH_2-CH_2-$ |
| $NO_2$ | ![phenyl with CF3] | $CH_3$ | H | H |
| $NO_2$ | ![phenyl with Cl, Cl] | $-CO-CH_3$ | H | H |
| $NO_2$ | ![phenyl with Cl, Cl] | H | | $-CH_2-CH_2-$ |
| $NO_2$ | ![phenyl with NO2] | $-CO-CH_3$ | H | H |

-continued
| D | A | R² | R³ | R⁴ |
|---|---|---|---|---|
| NO₂ | 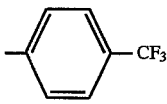 4-CF₃-phenyl | —CH₃ | H | H |
| NO₂ | 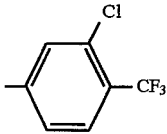 3-Cl-4-CF₃-phenyl | —CH₃ | H | H |
| NO₂ | 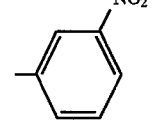 3-NO₂-phenyl | H | | —CH₂—CH₂— |
| NO₂ | 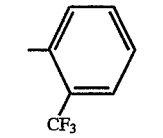 2-CF₃-phenyl | —CO—CH₃ | H | H |
| NO₂ | 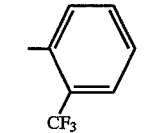 2-CF₃-phenyl | H | | —CH₂—CH₂— |
| NO₂ | 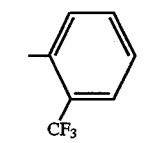 2-CF₃-phenyl | CH₃ | H | H |
| NO₂ | 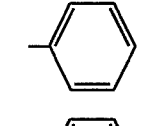 phenyl | —CO—CH₃ | H | H |
| NO₂ | 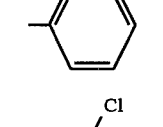 phenyl | H | | —CH₂—CH₂— |
| NO₂ | 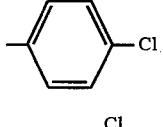 3,4-diCl-phenyl | H | H | H |
| NO₂ | 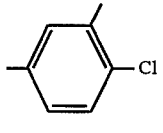 3,4-diCl-phenyl | —CO—CH₃ | H | H |
| NO₂ | 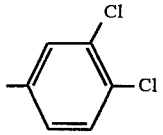 3,4-diCl-phenyl | H | | —CH₂—CH₂— |
| NO₂ | 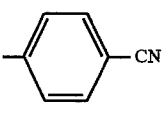 4-CN-phenyl | H | H | H |

-continued

| D | A | R² | R³ | R⁴ |
|---|---|---|---|---|
| NO₂ | 4-CN-phenyl | H | | —CH₂—CH₂— |
| NO₂ | 4-CN-phenyl | —CO—CH₃ | H | H |
| NO₂ | 3-F, 4-OCH₃-phenyl | —CO—CH₃ | H | H |
| CN | phenyl | H | H | H |
| CN | 2,3-diCl-phenyl | —CO—CH₃ | H | H |
| CN | 2,3-diCl-phenyl | CH₃ | H | H |
| CN | 4-CF₃-phenyl | H | H | H |
| CN | 4-Cl-phenyl | H | H | H |
| CN | 4-OCH₃-phenyl | H | H | H |
| CN | 4-CF₃-phenyl | H | H | H |
| CN | 3-NO₂-phenyl | H | H | H |
| CN | 4-Cl-phenyl | H | H | H |
| CN | 2-CF₃-phenyl | H | H | H |

-continued

| D | A | R² | R³ | R⁴ |
|---|---|---|---|---|
| CN | 4-biphenylyl | H | H | H |
| CN | 2-(trifluoromethyl)phenyl | CH₃ | H | H |
| CN | 3-nitrophenyl | CH₃ | H | H |
| CN | 4-chlorophenyl | CH₃ | H | H |
| CN | phenyl | CH₃ | H | H |

The compounds according to the invention and the new substances of the general formula (I) can be prepared by a process in which compounds of the general formula (II)

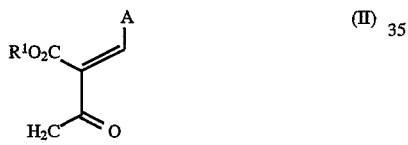

(II)

in which

A and $R^1$ have the abovementioned meaning but
$R^1$ does not represent hydrogen,
in the case where $D=NO_2$, are reacted with compounds of the general formula (III)

(III)

in which $R^2$ and $R^3$ have the abovementioned meaning,
and in the case where D=CN, are reacted with compounds of the general formula (IV) ($R^2/R^3=H$)

(IV)

in which

Z represents $C_1$–$C_4$-alkyl, in organic solvents, if appropriate in the presence of an ammonium salt, preferably ammonium acetate, and in the case where $R^2$ and/or $R^3 \neq H$, the product is reacted with the corresponding alcoholic amine solution, or if appropriate an alkylation or acylation is carried out, in organic solvents and in the presence of a base, and in the case where $R^1=H$, the esters are hydrolysed by customary methods.

The process according to the invention can be illustrated by way of example by the following equation:

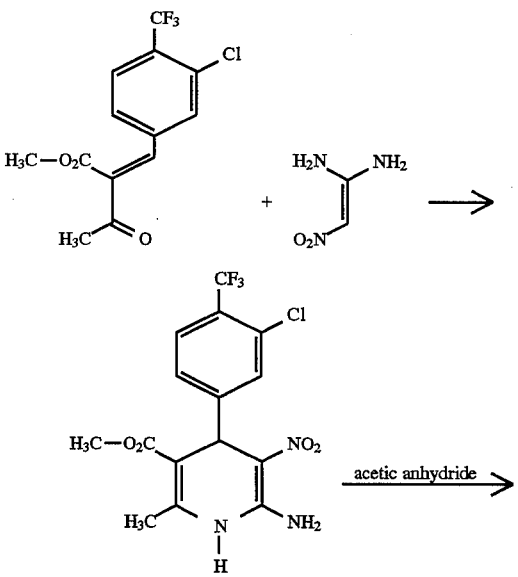

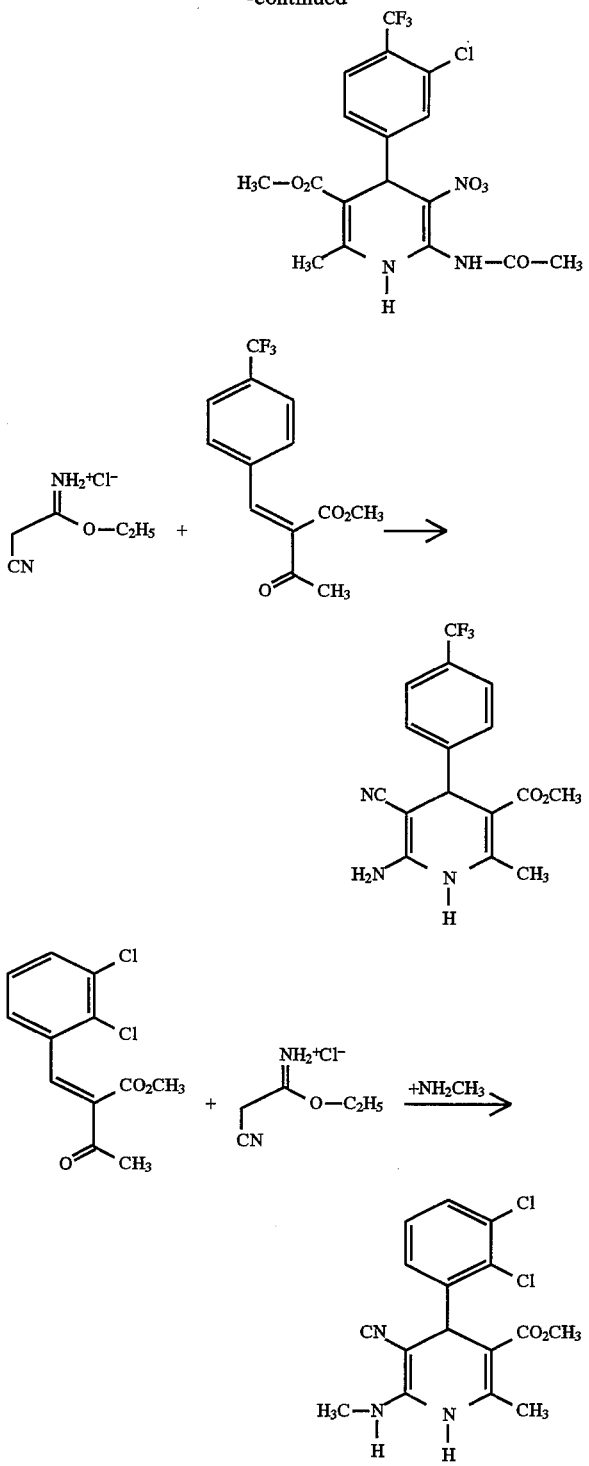

-continued

Suitable solvents here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, acetonitrile, or amides, such as hexamethylphosphoric acid triamide or dimethylformamide, or acetic acid or halogenated hydrocarbons, such as methylene chloride or carbon tetrachloride, or hydrocarbons, such as benzene or toluene. It is also possible to use mixtures of the solvents mentioned. Isopropanol, ethanol, tetrahydrofuran, methanol, dioxane and dimethylformamide are particularly preferred.

Suitable bases are in general alkali metal hydrides or alcoholates, such as, for example, sodium hydride or potassium tert-butylate, or cyclic amines, such as, for example, piperidine or dimethylaminopyridine, or $C_1$–$C_4$-alkylamines, such as, for example, triethylamine. Piperidine, dimethylaminopyridine, pyridine, sodium hydride and potassium tert-butylate are preferred.

The substances participating in the reaction can be used in any desired ratio in carrying out the processes according to the invention. In general, however, equimolar amounts of the reactants are used.

The reaction temperatures can be varied within a relatively wide range. In general, the reaction is carried out at between +10° C. and +150° C., preferably between +20° C. and +100° C., in particular at the boiling point of the particular solvent.

The reactions can be carried out under normal pressure, or else under increased or reduced pressure (for example 0.5 to 3 bar). The reactions are in general carried out under normal pressure.

Suitable solvents for the alkylation are likewise customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, or triethylamine, pyridine, dimethyl sulphoxide, dimethylformamide, hexamethylphosphoric acid triamide, acetonitrile, acetone or nitromethane. It is also possible to use mixtures of the solvents mentioned. Dimethylformamide is preferred.

Suitable bases are in general alkali metal hydrides or alcoholates, such as, for example sodium hydride or potassium tert-butylate, or cyclic amines, such as, for example, piperidine or dimethylaminopyridine, or $C_1$–$C_4$-alkylamines, such as, for example, triethylamine. Sodium hydride is preferred.

The reaction temperatures can be varied within a relatively wide range. In general, the reaction is carried out at between +10° C. and +150° C., preferably between +20° C. and 100° C., in particular at room temperature.

The alkylation is carried out in the abovementioned solvents at temperatures of 0° C. to +150° C., preferably at room temperatures up to +100° C.

The reactions can be carried out under normal pressure, or else under increased or reduced pressure (for example 0.5 to 3 bar). They are in general carried out under normal pressure.

The base is in general employed in an amount of 1 mol to 5 mol, preferably 1 mol to 2 mol, in each case per mol of the compounds to be alkylated.

Suitable bases for the acylation are organic bases, such as, for example, organic tertiary amines, trialkyl($C_1$–$C_6$)amines, such as triethylamine, or heterocyclic compounds, such as pyridine, 4-(N,N-dimethylamino)pyridine or methylpiperidine. Triethylamine is particularly preferred.

Suitable solvents for the acylation are likewise customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, or triethylamine, pyridine, dimethyl sulphoxide, dimethylformamide, hexamethylphosphoric acid triamide, acetonitrile, acetone or nitromethane. It is also possible to use mixtures of the solvents mentioned or else to employ the particular acylating agent as the solvent. Acetic anhydride and pyridine are preferred.

The acylation in general proceeds in a temperature range from 0° C. to +120° C., preferably at +30° C. to +90° C. and under normal pressure.

The hydrolysis of the carboxylic acid esters is carried out by customary methods by treating the esters with customary bases in inert solvent.

Suitable bases for the hydrolysis are the customary inorganic bases. These include, preferably, alkali metal hydroxide or alkaline earth metal hydroxides, such as, for example, sodium hydroxide, potassium hydroxide or barium hydroxide, or alkali metal carbonates, such as sodium carbonate or potassium carbonate, or sodium bicarbonate. Sodium hydroxide or potassium hydroxide is particularly preferably employed.

Suitable solvents for the hydrolysis are water or the organic solvents customary for a hydrolysis. These include, preferably, alcohols, such as methanol, ethanol, propanol, isopropanol or butanol, or ethers such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure. (for example from 0.5 to 5 bar).

Enantiomerically pure forms are obtained, for example, by a procedure in which diastereomer mixtures of the compounds of the general formula (I) are separated by the customary method and the diastereomers are then either transesterified directly or the chiral carboxylic acids are first prepared and the enantiomerically pure dihydropyridines are then prepared by esterification.

The diastereomers are in general separated either by fractional crystallization, by column chromatography or by Craig partition. The optimum process must be decided from case to case, and sometimes it is also expedient to use combinations of the individual processes. Separation by crystallization or Craig partition or by a combination of the two processes is particularly suitable.

The enantiomerically pure compounds are also accessible by chromatography or the racemic esters on chiral phases.

The compounds of the general formula (II), (III) and (IV) are known or can be prepared by customary methods.

The compounds of the general formula (I) according to the invention display a valuable unforeseeable action spectrum, in particular on the basis of their selectivity for large conductance for calcium-dependent potassium channels.

$^{86}$Rubidium efflux from C6-BU1 glioma cells

The experiments were carried out in accordance with the method described by Tas et al. (Neurosci. Lett. 94, 279–284, (1988)), with slight changes. Rat C6-BU1 glioma cell cultures were used for the experiments. The increase in the $^{86}$ rubidium efflux above the basal efflux produced by ionomycin is calculated from the data and set at 100 %. The stimulations in the presence of test substances are then based on this value.

The present invention also relates to pharmaceutical formulations which, in addition to inert, non-toxic, pharmaceutically suitable auxiliaries and excipients, comprise one or more compounds of the general formula (I), or which consist of one or more active compounds of the formula (I), and to processes for the preparation of these formulations.

The active compounds of the formula (I) should be present in these formulations in a concentration of 0.1 to 99.5 % by weight, preferably 0.5 to 95 % by weight of the total mixture.

In addition to the active compounds of the formula (I), the pharmaceutical formulations can also comprise other pharmaceutical active compounds.

The abovementioned pharmaceutical formulations can be prepared in the customary manner by known methods, for example with the auxiliary or excipient substance or substances.

In general, it has proved advantageous to administer the active compound or compounds of the formula (I) in total amounts of about 0.01 to about 100 mg/kg, preferably in total amounts of about 1 mg/kg to 50 mg/kg of body weight every 24 hours, if appropriate in the form of several individual doses, in order to achieve the desired result.

Where appropriate, however, it may be advantageous to deviate from the amounts mentioned, and in particular as a function of the nature and body weight of the subject treated, of the behaviour of the individual towards the medicament, of the nature and severity of the disease, of the nature of the formulation and administration, and of the time or interval at which administration takes place.

Starting compounds

EXAMPLE I

Methyl 2-acetyl-3-(3-chloro-4-trifluoromethylphenyl)acrylate

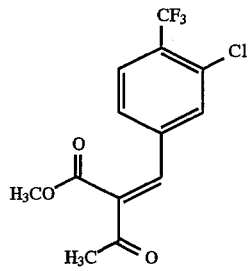

32.3 g (155 mol) of 3-chloro-4-trifluoromethylbenzaldehyde and 18.0 g (155 mmol) of methyl acetoacetate are dissolved in 200 ml of methylene chloride, and 1.2 ml of piperidine and 1 ml of glacial acetic acid are added. The mixture is heated for 5 hours, using a water separator. It is then washed with water, dried over MgSO$_4$ and concentrated. The product is recrystallized twice from methanol. 25.6 g (54% of theory) of the title compound are obtained.

EXAMPLE II

1-N-methylamino-2-nitro-ethylene-1-amine

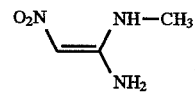

25.0 g (0.15 mol) of 1,2-bis(methylthio)-2-nitroethane are dissolved in 300 ml of ethanol, and 11.9 g (0.18 mol) of methylamine hydrochloride are added. The mixture is heated to the reflux temperature and 4 portions of 20.2 g (0.18 mol) of potassium tert-butylate in total are added every 30 minutes. The mixture is then kept under reflux for 1 hour (thin layer chromatography control: ethyl acetoacetate/ petroleum ether 3:1). It is concentrated, the residue is taken up in methylene chloride and the mixture is washed with water and dried over sodium sulphate. It is then concentrated and the residue is filtered over silica gel (methylene chloride). The product is crystallized from ethanol. The solid which has been isolated is then dissolved in 200 ml of butanol, and ammonia is passed into the solution under reflux for 2 hours (thin layer chromatography control). The solvent is distilled off and the residue is crystallized from ethanol.

Yield: 2.9 g (16% of theory)

Preparation examples

Example 1

Methyl 6-amino-4-(3-chloro-4-trifluoromethylphenyl)-1,4-dihydro-2-methyl-5-nitro-3-carboxylate

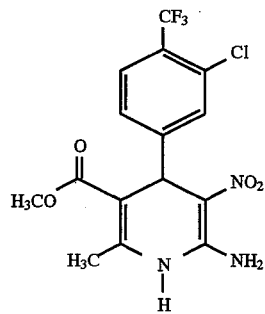

15.3 g (50 mmol) of the compound from Example I and 5.2 g (50 mmol) of 2-nitro-1,1-ethenediamine are dissolved in 80 ml of ethanol and the solution is kept under reflux for 12 hours. After cooling, the solid which has formed is filtered off with suction and washed with ethanol. 13.0 g (66% of theory) of the title compound are obtained.

Melting point: 250° C.

The compounds shown in Table 1 are prepared analogously to the instructions of Example 1:

TABLE 1

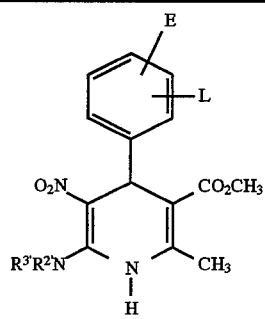

| Example No. | E, L | R2' | R3' | Yield (% of theory) | Melting point (°C.) |
|---|---|---|---|---|---|
| 2 | 3-H, 4-CF3 | H | H | 35 | 260 |
| 3 | 3-Cl, 4-Cl | H | H | 40 | 254–6 |
| 4 | 3-H, 4-CN | H | H | 45 | 266–70 |

Example 5

Methyl 6-acetylamino-4-(3-chloro-4-trifluoromethylphenyl)-1,4-dihydro-2-methyl-3-nitro-5-carboxylate

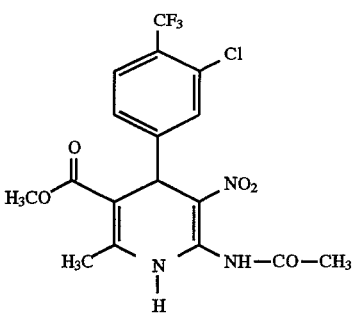

4.0 g (10.2 mmol) of the compound from Example 1 are dissolved in 40 ml of acetic anhydride and the mixture is heated under reflux for 12 hours. The acetic anhydride is then distilled off under reduced pressure, the residue is dissolved in methylene chloride and the mixture is washed with saturated aqueous NaHCO3 solution. The organic phase is dried (MgSO4) and concentrated and the residue is purified by chromatography on silica gel (toluene/AcOEt/iPrOH 100+10+1). The concentrated eluate is recrystallized from ethanol. 0.5 g (11% of theory) of the title compound is obtained.

Melting point: 152° C.

The compounds shown in Table 2 are prepared analogously to the instructions of Example 5:

TABLE 2

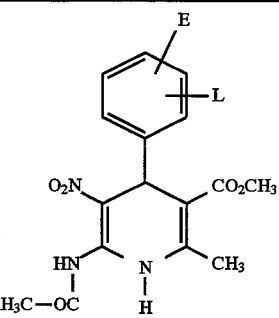

| Example No. | E, L | Yield (% of theory) | Melting point (°C.) |
|---|---|---|---|
| 6 | 3-H, 4-CF3 | 22 | 135–6 |
| 7 | 2-Cl, 3-Cl | 54 | 214–6 |
| 8 | 3-NO2, 4-H | 66 | 205–6 |
| 9 | 2-CF3, 3-H | 44 | 195 |
| 10 | 3-H, 4-H | 43 | 200–2 |
| 11 | 3-Cl, 4-Cl | 22 | 174–5 |
| 12 | 3-CN, H | 62 | 160–1 |
| 13 | 4-OCH3, H | 13 | 210 |

Example 14

4-(2,3-Dichlorophenyl)-3-methoxycarbonyl-2-methyl-3-nitro-1,7-diaza-[4.3.0]bicyclonona-2,4-diene

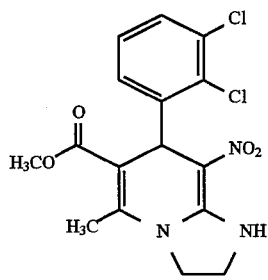

5.7 g (20 mmol) of 2-acetyl-3(2,3-dichlorophenyl)acrylic acid methyl ester and 2.6 g (20 mmol) of 2-nitromethylene-1,3-diazolidine are dissolved in 30 ml of ethanol and the solution is heated at 80° C. for 18 hours. After cooling, the solid formed is filtered off with suction and washed with ethanol. It is then suspended in toluene, 20 mg of p-toluenesulphonic acid are added and the mixture is kept under reflux for 18 hours, using a water separator. The solid which crystallizes out on cooling is filtered off with suction. 6.1 g (79% of theory) of the title compound are obtained.

Melting point: 225° C.

The compounds shown in Table 3 are prepared analogously to the instructions of Example 14.

Example 22

Methyl 1,4-dihydro-2-methyl-6-methylamino-4-(3-chloro-4-trifluoromethylphenyl)-5-nitro-3-carboxylate

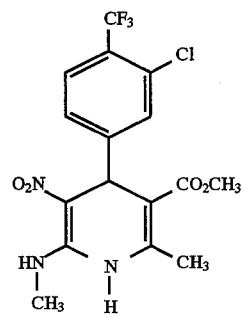

2.9 g (25 mmol) of 1-N-methylamino-2-nitroethylene-1-amine and 6.7 g (25 mmol) of methyl 2-acetyl-3-(3-chloro-4-trifluoromethylphenyl)acrylate are dissolved in 100 ml of ethanol and the solution is heated under reflux overnight. The reaction mixture is concentrated and the residue is chromatographed twice over silica gel (1: methylene chloride: AcOEt (gradient), 2: methylene chloride: MeOH 100+1). 1.2 g (21.6% of theory) of the title compound are obtained after recrystallization from EtOH/acetonitrile.

The compounds shown in Table 4 are prepared analogously to the instructions of Example 22.

TABLE 3

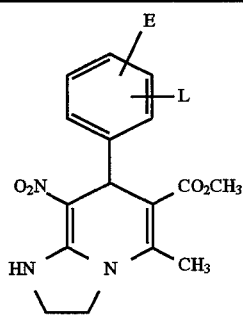

| Example No. | E, L | Yield (% of theory) | Melting point (°C.) |
|---|---|---|---|
| 15 | 3-H, 4-CF₃ | 8 | 183–4 |
| 16 | 3-Cl, 4-CF₃ | 40 | 207–8 |
| 17 | 3-NO₂, 4-H | 60 | 257–8 |
| 18 | 2-CF₃, 3-H | 40 | 248–9 |
| 19 | H, H | 67 | 226–7 |
| 20 | 3-Cl, 4-Cl | 25 | 221–2 |
| 21 | 3-H, 4-CN | 84 | 253–5 |

TABLE 4

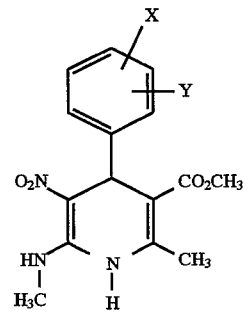

| Example No. | X, Y | Yield (% of theory) | Melting point (°C.) |
|---|---|---|---|
| 23 | 4-CF₃, H | 61 | 210–2 |
| 24 | 2-CF₃, H | 15 | 211–2 |

Example 25

Methyl 6-amino-5-cyano-2-methyl-4-(4-trifluoromethylphenyl)-1,4-dihydropyridine-3-carboxylate

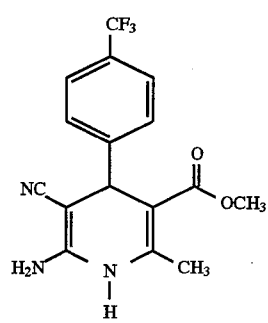

13.6 g (50 mmol) of methyl 2-acetyl-3-(4-trifluoromethylphenyl)acrylate, 7.45 g (50 mmol) of cyanoacetimide acid ethyl ester hydrochloride and 15 g (190 mmol) of ammonium acetate are heated under reflux in 100 ml of methanol for 1 hour. After the mixture has been concentrated, the residue is partitioned between ice-water and ethyl acetate. The organic phase is washed twice with dilute aqueous $NaHCO_3$ solution and once with water, dried over $Na_2CO_3$ and concentrated in vacuo. Crystallization of the residue (18.4 g) from methanol gives 6.3 g (37% of theory) of colourless crystals of the title compound.

Melting point: 210°–214° C.

The compounds shown in Table 5 are prepared analogously to the instructions of Example 25:

TABLE 5

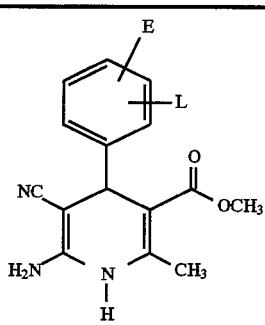

| Example No. | E, L | Yield (% of theory) | Melting point (°C.)/$R_f$ |
|---|---|---|---|
| 26 | 3-H, 4-Cl | 25 | 188–90/ 0.19 (tol:AcOEt 1:1) |
| 27 | H, H | 40 | 208–9 0.39 (AcOEt) |
| 28 | 4-OCH₃ | 22 | 203–5 |

Example 29

Methyl 6-acetamido-5-cyano-4-(2,3-dichlorophenyl)-2-methyl-1,4-dihydropyridine-3-carboxylate

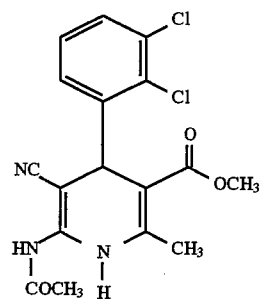

6.7 g (20 mmol) of methyl 6-amino-5-cyano-4-(2,3-dichlorophenyl)-2-methyl-1,4-dihydropyridine-3-carboxylate and 33.5 ml (350 mmol) of acetic anhydride are heated under reflux for 30 minutes. Excess acetic anhydride is then converted into methyl acetate by addition of methanol at 25° C., while stirring. The reaction solution is evaporated in vacuo and toluene is then shipped off from the residue twice in vacuo. The residue is then boiled up with 50 ml of toluene. The crystals which have separated out are filtered off and washed with toluene.

Yield: 3.6 g (50% of theory)

Melting point: 224° C. (decomposition)

The compounds shown in Table 6 are prepared analogously to the instructions of Example 29:

TABLE 6

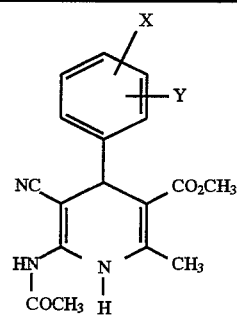

| Example No. | X, Y | Yield (% of theory) | Melting point (°C.) |
|---|---|---|---|
| 30 | 4-CF₃, H | 20 | 160–64 |
| 31 | 3-NO₂, H | 42 | 288 decomp. |
| 32 | 4-Cl, H | 20 | 177 |
| 33 | H | 50 | 211–2 |
| 34 | 2-CF₃, H | 22 | 220–3 |
| 35 | 4-C₆H₅, H | 35 | 196–7 |

Example 36

Methyl 5-cyano-4-(2,3-dichlorophenyl)-2-methyl-6-N-methylamino-1,4-dihydropyridine-3-carboxylate

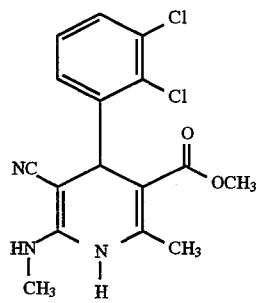

5 ml (33% strength) of ethanolic methylamine solution (40 mmol) are added to 2.8 g (10 mmol) of methyl 2-acetyl-3-(2,3-dichlorophenyl)acrylate and 1.5 g (10 mmol) of cyanoacetimide acid ethyl ester hydrochloride. The mixture is warmed to 46° C. After cooling to 30° C., 23 ml (40 mmol) of glacial acetic acid and then 20 ml of methanol are added. After heating under reflux for 5 hours, ice-water is added to the reaction solution and the mixture is extracted with ethyl acetoacetate. Drying of the organic phase (Na₂SO₄) and concentration under reduced pressure gives 3.9 g of amorphous residue, which is chromatographed over 100 g of silica gel using toluene/ethyl acetoacetate (gradient).

Yield: 0.5 g (10% of theory) of crystals

Melting point: 234°–239° C.

The compounds shown in Table 7 are prepared analogously to the instructions of Example 36:

TABLE 7

| Example No. | X, Y | Yield (% of theory) | Melting point (°C.) |
|---|---|---|---|
| 37 | 2-CF₃, H | 12 | 216–9 |
| 38 | 3-NO₂, H | 15 | 178–81 |

TABLE 7-continued

| Example No. | X, Y | Yield (% of theory) | Melting point (°C.) |
|---|---|---|---|
| 39 | 4-Cl, H | 8 | oil |
| 40 | H, H | 16 | 168–71 |

We claim:

1. A method of treating diseases of the CNS by selectively modulating the potassium channels which comprises administering to a patient in need thereof an effective amount of a 6-amino-dihydropyridine of the formula (I)

in which

A represents aryl having 6 to 10 carbon atoms or pyridyl, each of which is optionally substituted up to 3-fold in an identical or different manner by nitro, cyano, phenyl, halogen, trifluoromethyl or by straight-chain or branched alkylthio or alkoxy having in each case up to 6 carbon atoms, D represents cyano or nitro, $R^1$ represents hydrogen, or represents straight-chain or branched alkyl having up to 8 carbon atoms, $R^2$ and $R^3$ are identical or different and represent hydrogen, or represent straight-chain or branched alkyl or acyl having in each case up to 6 carbon atoms, $R^4$ represents hydrogen, or $R^3$ and $R^4$ together represent a radical of the formula —(CH₂)ₙ—, wherein n denotes the number 2, 3 or 4, or physiologically acceptable salt thereof.

2. The method according to claim 1 wherein the compound is

| D | A | $R^2$ | $R^3$ | $R^4$ |
|---|---|---|---|---|
| NO₂ | 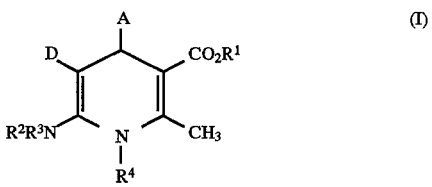 | H | H | H |

-continued
| D | A | R² | R³ | R⁴ |
|---|---|---|---|---|
| NO₂ | 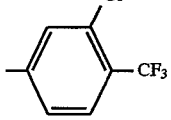 3-Cl, 4-CF₃ phenyl | —CO—CH₃ | H | H |
| NO₂ | 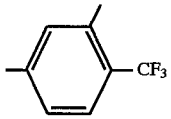 3-Cl, 4-CF₃ phenyl | H | \multicolumn{2}{l|}{—CH₂—CH₂—} |
| NO₂ | 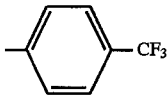 4-CF₃ phenyl | H | H | H |
| NO₂ | 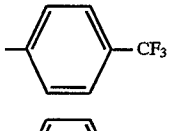 4-CF₃ phenyl | —CO—CH₃ | H | H |
| NO₂ | 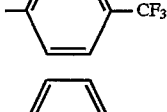 4-CF₃ phenyl | H | \multicolumn{2}{l|}{—CH₂—CH₂—} |
| NO₂ | 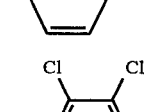 4-CF₃ phenyl | CH₃ | H | H |
| NO₂ | 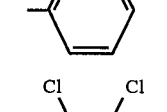 2,3-diCl phenyl | —CO—CH₃ | H | H |
| NO₂ | 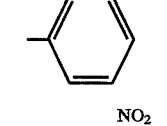 2,3-diCl phenyl | H | \multicolumn{2}{l|}{—CH₂—CH₂—} |
| NO₂ | 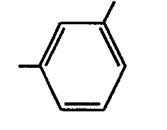 3-NO₂ phenyl | —CO—CH₃ | H | H |
| NO₂ | 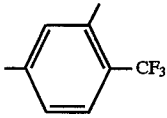 3-Cl, 4-CF₃ phenyl | —CH₃ | H | H |
| NO₂ | 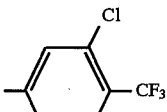 3-Cl, 4-CF₃ phenyl | —CH₃ | H | H |
| NO₂ | 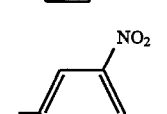 3-NO₂ phenyl | H | \multicolumn{2}{l|}{—CH₂—CH₂—} |

-continued

| D | A | R² | R³ | R⁴ |
|---|---|---|---|---|
| NO₂ | 2-CF₃-phenyl | —CO—CH₃ | H | H |
| NO₂ | 2-CF₃-phenyl | H | | —CH₂—CH₂— |
| NO₂ | 2-CF₃-phenyl | CH₃ | H | H |
| NO₂ | phenyl | —CO—CH₃ | H | H |
| NO₂ | phenyl | H | | —CH₂—CH₂— |
| NO₂ | 3,4-di-Cl-phenyl | H | H | H |
| NO₂ | 3,4-di-Cl-phenyl | —CO—CH₃ | H | H |
| NO₂ | 3,4-di-Cl-phenyl | H | | —CH₂—CH₂— |
| NO₂ | 4-CN-phenyl | H | H | H |
| NO₂ | 4-CN-phenyl | H | | —CH₂—CH₂— |
| NO₂ | 4-CN-phenyl | —CO—CH₃ | H | H |
| NO₂ | 3-F-4-OCH₃-phenyl | —CO—CH₃ | H | H |

-continued
| D | A | R² | R³ | R⁴ |
|---|---|---|---|---|
| CN | 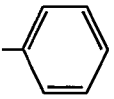 | H | H | H |
| CN | 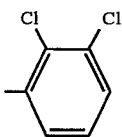 | —CO—CH₃ | H | H |
| CN | 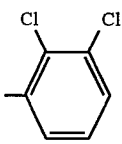 | CH₃ | H | H |
| CN | 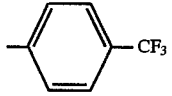 | H | H | H |
| CN | 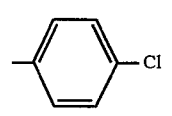 | H | H | H |
| CN | 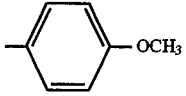 | H | H | H |
| CN | 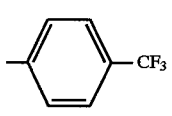 | H | H | H |
| CN | 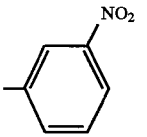 | H | H | H |
| CN | 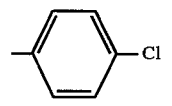 | H | H | H |
| CN | 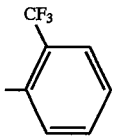 | H | H | H |
| CN | 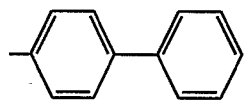 | H | H | H |
| CN | 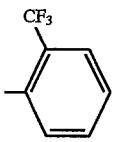 | CH₃ | H | H |

-continued

| D | A | $R^2$ | $R^3$ | $R^4$ |
|---|---|---|---|---|
| CN | (phenyl with NO₂) | $CH_3$ | H | H |
| CN | (phenyl with Cl) | $CH_3$ | H | H |
| CN | (phenyl) | $CH_3$ | H | H |

3. A 6-acylamino-dihydropyridine of the formula $$\begin{array}{c} A \\ D \diagdown \diagup CO_2R^1 \\ R^2R^3N \diagdown N \diagup CH_3 \\ | \\ R^4 \end{array} \quad (I)$$

in which

A represents aryl having 6 to 10 carbon atoms or pyridyl, each of which is optionally substituted up to 3-fold in an identical or different manner by nitro, cyano, phenyl, halogen, trifluoromethyl or by straight-chain or branched alkylthio or alkoxy having in each case up to 6 carbon atoms, D represents cyano or nitro, $R^1$ represents hydrogen, or represents straight-chain or branched alkyl having up to 8 carbon atoms, $R^2$ and $R^3$ are identical or different and represent hydrogen, or represent straight-chain or branched alkyl or acyl having in each case up to 6 carbon atoms, at least one of the substituents is an acyl group, $R^4$ represents hydrogen, or $R^3$ and $R^4$ together represent a radical of the formula —$(CH_2)_n$, wherein n denotes the number 2, 3 or 4, or physiologically acceptable salt thereof, with the proviso that compounds of the formula (structure shown: 2-nitro-biphenyl with propionyl group and fused ring containing $N-N-(CH_2)_n$)

where n is 2, 3 or 4 are excluded.

4. A compound according to claim 3, wherein

A represents phenyl or pyridyl, each of which is optionally substituted up to 2-fold in an identical or different manner by nitro, cyano, phenyl, fluorine, chlorine, trifluoromethyl, methoxy or methylthio, D represents cyano or nitro, $R^1$ represents straight-chain or branched alkyl having up to 4 carbon atoms, $R^2$ and $R^3$ are identical or different and represent hydrogen, or represent straight-chain or branched alkyl or acyl having in each case up to 4 carbon atoms, at least one of the substituents is acyl, $R^4$ represents hydrogen, or $R^3$ and $R^4$ together represent an ethylene or propylene radical, or a salt thereof.

5. A pharmaceutical composition which comprises an effective amount of a compound according to claim 3 and an inert carrier.

6. A process for the preparation of the compounds of claim 3, said process comprising reacting a compound of the formula $$\begin{array}{c} A \\ R^1O_2C \diagdown \diagup \\ H_3C \diagup \diagdown O \end{array} \quad (II)$$

in which

A and $R^1$ have the abovementioned meaning but $R^1$ does not represent hydrogen, in the case where D is $NO_2$, with a compound of the formula $$\begin{array}{c} R^2R^3N \diagdown \diagup NH_2 \\ O_2N \diagup \end{array} \quad (III)$$

in which $R^2$ and $R^3$ have the abovementioned meaning, or in the case where D is CN, with a compound of the formula $$\begin{array}{c} H_2N^+Cl^- \\ \diagdown \diagup O-Z \\ CN \end{array} \quad (IV)$$

in which

Z represents $C_1$–$C_4$-alkyl, in the presence of an organic solvent and optionally in the presence of an ammonium salt, and the resulting product is reacted with the corresponding alcoholic amino solution followed optionally with an alkylation or an acylation, in the presence of a base and in the presence of an organic solvent.

7. The process according to claim 5, wherein the ammonium salt is ammonium acetate.

8. A compound according to claim 3, wherein R² is an acyl group.

9. A compound according to claim 3, of the formula

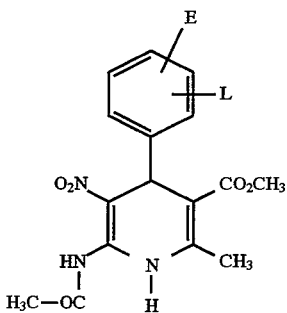

wherein

E, L represents 3-H, 4-CF₃; 2-Cl, 3Cl; 3-NO₂, 4-H; 2-CF₃, 3-H; 3-H, 4-H; 3-Cl, 4-Cl; 4-CN, H or 4-OCH₃, H.

10. The compound according to claim 3, which has the formula

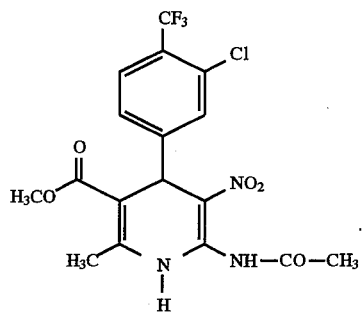

11. A compound according to claim 3, of the formula

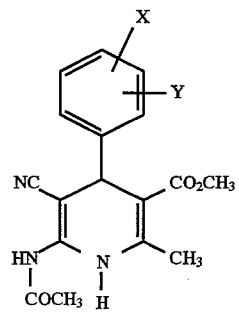

wherein

X, Y represents 4-CF₃, H; 3-NO₂, H; 4-Cl, H; H; 2-CF₃, H, or 4-C₆H₅, H.

12. The compound according to claim 3, which has the formula

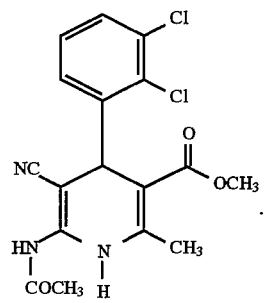

13. The method according to claim 1, wherein the disease is dementia.

14. The method according to claim 1, wherein the disease is depression.

15. The method according to claim 1, wherein the disease is a psychoses.

16. The method according to claim 7, wherein the diseases are cerebral ischaemias.

* * * * *

UNITED STATES PATENT AND TRADEMARK OFFICE
CERTIFICATE OF CORRECTION

PATENT NO.  : 5,652,251                                           Page 1 of 2
DATED       : July 29, 1997
INVENTOR(S) : Urbahns, et al.

It is certified that error appears in the above-identified patent and that said Letters Patent is hereby corrected as shown below:

Col. 23, line 10   Under " A " delete " 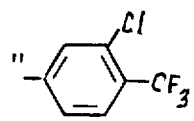 " and substitute -- 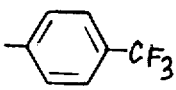 --

Col. 29, line 57   Delete " 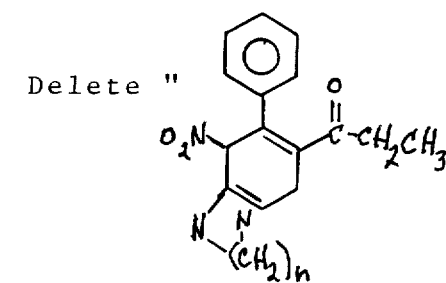 " and substitute

-- 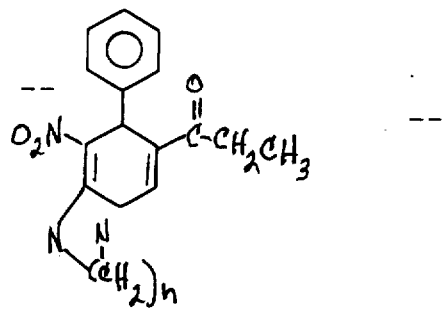 --

UNITED STATES PATENT AND TRADEMARK OFFICE
CERTIFICATE OF CORRECTION

PATENT NO. : 5,652,251
DATED : July 29, 1997
INVENTOR(S) : Urbahns, et al.

It is certified that error appears in the above-identified patent and that said Letters Patent is hereby corrected as shown below:

Col. 29, line 65    Delete " A " and substitute -- The --

Signed and Sealed this

Seventeenth Day of February, 1998

Attest:

BRUCE LEHMAN

Attesting Officer

Commissioner of Patents and Trademarks